(12) United States Patent
Woolford et al.

(10) Patent No.: US 12,042,664 B2
(45) Date of Patent: *Jul. 23, 2024

(54) INTEGRATED PUMP CONTROL FOR DYNAMIC CONTROL OF PLASMA FIELD

(71) Applicant: Stryker Corporation, Kalamazoo, MI (US)

(72) Inventors: Brady L. Woolford, Mapleton, UT (US); Brian Fouts, Morgan Hill, CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/139,698

(22) Filed: Apr. 26, 2023

(65) Prior Publication Data

US 2023/0347159 A1 Nov. 2, 2023

Related U.S. Application Data

(60) Continuation of application No. 16/690,418, filed on Nov. 21, 2019, now Pat. No. 11,660,460, which is a
(Continued)

(51) Int. Cl.
*A61N 1/44* (2006.01)
*A61B 18/04* (2006.01)
(Continued)

(52) U.S. Cl.
CPC .............. *A61N 1/44* (2013.01); *A61B 18/042* (2013.01); *A61B 18/1206* (2013.01); *A61M 1/74* (2021.05);
(Continued)

(58) Field of Classification Search
CPC ............ A61M 1/64; A61M 1/65; A61M 1/71; A61M 1/72; A61M 1/74; A61M 1/77;
(Continued)

(56) References Cited

U.S. PATENT DOCUMENTS 4,222,391 A 9/1980 Rawson et al.
4,902,277 A 2/1990 Mathies et al.
(Continued)

FOREIGN PATENT DOCUMENTS

EP 1263341 B1 6/2008
EP 1946716 A1 7/2008
(Continued)

OTHER PUBLICATIONS

"Flocontrol Arthroscopy Pump Manual", published in 2004, pp. 1-52 (60 pages).
(Continued)

*Primary Examiner* — Kevin C Sirmons
*Assistant Examiner* — Alexandra Lalonde
(74) *Attorney, Agent, or Firm* — Lerner David LLP

(57) ABSTRACT

A pump and a pump controller which uses an algorithm to quickly achieve and maintain a stable plasma field in a surgical site are provided. The algorithm calculates an electrical characteristic value to determine if a suction rate by the pump should be increased or decreased to achieve the stable plasma field. A method of using the pump and the pump controller is also provided.

20 Claims, 4 Drawing Sheets

Related U.S. Application Data division of application No. 15/292,496, filed on Oct. 13, 2016, now abandoned.

(60) Provisional application No. 62/242,529, filed on Oct. 16, 2015.

(51) Int. Cl.
    *A61B 18/12*     (2006.01)
    *A61M 1/00*     (2006.01)
    *A61M 3/02*     (2006.01)
    *A61B 18/00*     (2006.01)

(52) U.S. Cl.
CPC .......... *A61M 1/743* (2021.05); *A61M 3/0233* (2013.01); *A61B 2018/00577* (2013.01); *A61B 2018/00666* (2013.01); *A61B 2018/00744* (2013.01); *A61B 2018/00892* (2013.01); *A61B 2218/007* (2013.01); *A61M 3/0201* (2021.05); *A61M 3/0202* (2021.05); *A61M 3/0208* (2014.02); *A61M 3/022* (2014.02); *A61M 2205/3334* (2013.01)

(58) Field of Classification Search
CPC ...... A61M 1/741; A61M 1/774; A61M 1/743; A61M 1/00; A61M 1/80; A61M 1/892; A61M 1/804; A61M 1/81; A61M 1/815; A61M 1/82; A61M 1/90; A61M 1/92; A61M 1/96; A61M 3/0283; A61M 3/022; A61M 3/0202; A61M 3/02; A61M 2205/3334; A61M 1/66; A61M 1/67; A61M 1/68; A61M 1/682; A61M 1/684; A61M 1/7411; A61M 1/7413; A61M 1/7415; A61M 1/742; A61M 1/75; A61M 1/76; A61M 1/772; A61M 1/802; A61M 1/84; A61M 1/86; A61M 1/91; A61M 1/962; A61M 3/0208; A61M 3/0201; A61M 2205/3327; A61M 2205/3337; A61M 2202/0014; A61M 1/85; A61M 3/0233; A61M 3/0254; A61M 3/0258; A61M 2205/50; A61M 2205/3379; A61M 2205/3331; A61M 2205/33; A61B 2018/00666; A61B 2018/00577; A61B 2018/00583; A61B 2018/1472; A61B 2018/00571; A61B 2018/00636; A61B 2018/00672; A61B 2018/00678; A61B 2018/00696; A61B 2018/00744; A61B 2218/001; A61B 2218/007; A61B 2018/00892; A61N 1/44

See application file for complete search history.

(56) References Cited

U.S. PATENT DOCUMENTS

| | | |
|---|---|---|
| 4,979,940 A | 12/1990 | Bobo, Jr. et al. |
| 5,000,733 A | 3/1991 | Mathies et al. |
| 5,334,193 A | 8/1994 | Nardella |
| 5,399,160 A | 3/1995 | Dunberger et al. |
| 5,520,638 A | 5/1996 | O'Quinn et al. |
| 5,542,928 A | 8/1996 | Evans et al. |
| 5,630,798 A | 5/1997 | Beiser et al. |
| 5,630,799 A | 5/1997 | Beiser et al. |
| 5,662,611 A | 9/1997 | Beiser et al. |
| 5,882,339 A | 3/1999 | Beiser et al. |
| 5,892,160 A | 4/1999 | Hall |
| 5,897,553 A | 4/1999 | Mulier et al. |
| 5,959,557 A | 9/1999 | Lim |
| 6,063,081 A | 5/2000 | Mulier et al. |
| 6,086,542 A | 7/2000 | Glowa et al. |
| 6,162,194 A | 12/2000 | Shipp |
| 6,295,877 B1 | 10/2001 | Aboul-Hosn et al. |
| 6,328,736 B1 | 12/2001 | Mulier et al. |
| 6,358,248 B1 | 3/2002 | Mulier et al. |
| 6,396,583 B1 | 5/2002 | Clare |
| 6,409,722 B1 | 6/2002 | Hoey et al. |
| 6,468,059 B2 | 10/2002 | Haser et al. |
| 6,475,216 B2 | 11/2002 | Mulier et al. |
| 6,500,175 B1 | 12/2002 | Gough et al. |
| 6,537,272 B2 | 3/2003 | Christopherson et al. |
| 6,585,732 B2 | 7/2003 | Mulier et al. |
| 6,626,355 B2 | 9/2003 | Sasse et al. |
| 6,699,244 B2 | 3/2004 | Carranza et al. |
| 6,702,810 B2 | 3/2004 | McClurken et al. |
| 6,716,211 B2 | 4/2004 | Mulier et al. |
| 6,736,810 B2 | 5/2004 | Hoey et al. |
| 6,764,487 B2 | 7/2004 | Mulier et al. |
| 6,849,073 B2 | 2/2005 | Hoey et al. |
| 6,896,664 B2 | 5/2005 | Novak |
| 6,949,098 B2 | 9/2005 | Mulier et al. |
| 7,150,713 B2 | 12/2006 | Shener et al. |
| 7,166,105 B2 | 1/2007 | Mulier et al. |
| 7,169,144 B2 | 1/2007 | Hoey et al. |
| 7,247,155 B2 | 7/2007 | Hoey et al. |
| 7,273,359 B2 | 9/2007 | Blight et al. |
| 7,287,968 B2 | 10/2007 | Haser et al. |
| 7,297,143 B2 | 11/2007 | Woloszko et al. |
| 7,364,579 B2 | 4/2008 | Mulier et al. |
| 7,371,224 B2 | 5/2008 | Haischmann et al. |
| 7,422,588 B2 | 9/2008 | Mulier et al. |
| 7,445,596 B2 | 11/2008 | Kucklick et al. |
| 7,503,893 B2 | 3/2009 | Kucklick |
| 7,510,542 B2 | 3/2009 | Blight |
| 7,526,960 B2 | 5/2009 | Francisco et al. |
| 7,604,610 B2 | 10/2009 | Shener et al. |
| 7,661,582 B2 | 2/2010 | Mollstam |
| 7,678,070 B2 | 3/2010 | Kumar et al. |
| 7,794,460 B2 | 9/2010 | Mulier et al. |
| 7,811,282 B2 | 10/2010 | McClurken |
| 7,815,634 B2 | 10/2010 | McClurken et al. |
| 7,981,073 B2 | 7/2011 | Mollstam et al. |
| 8,083,736 B2 | 12/2011 | McClurken et al. |
| 8,123,676 B2 | 2/2012 | Kucklick |
| 8,192,424 B2 | 6/2012 | Woloszko |
| 8,206,342 B2 | 6/2012 | Hacker et al. |
| 8,262,603 B2 | 9/2012 | Shener et al. |
| 8,355,799 B2 | 1/2013 | Marion et al. |
| 8,361,068 B2 | 1/2013 | McClurken |
| 8,372,067 B2 | 2/2013 | Woloszko et al. |
| 8,444,638 B2 | 5/2013 | Woloszko et al. |
| 8,696,659 B2 | 4/2014 | Marion |
| 8,852,184 B2 | 10/2014 | Kucklick |
| 8,870,866 B2 | 10/2014 | Woloszko |
| 8,979,838 B2 | 3/2015 | Woloszko et al. |
| 9,254,164 B2 | 2/2016 | Woloszko |
| 9,289,110 B2 | 3/2016 | Woolford et al. |
| 9,333,024 B2 | 5/2016 | Woloszko et al. |
| 9,358,063 B2 | 6/2016 | Marion |
| 9,452,008 B2 | 9/2016 | Marion et al. |
| 9,579,144 B2 | 2/2017 | Marion |
| 9,585,711 B2 | 3/2017 | Marion |
| 9,597,142 B2 | 3/2017 | Yuan et al. |
| 9,603,990 B2 | 3/2017 | Woolford |
| 9,649,148 B2 | 5/2017 | Woloszko et al. |
| 9,713,489 B2 | 7/2017 | Woloszko et al. |
| 9,770,282 B2 | 9/2017 | Hoey et al. |
| 9,801,678 B2 | 10/2017 | Cox |
| 11,660,460 B2 * | 5/2023 | Woolford ............ A61B 18/042 604/23 |
| 2003/0130577 A1 | 7/2003 | Purdy et al. |
| 2003/0208193 A1 | 11/2003 | Van Wyk |
| 2004/0006263 A1 | 1/2004 | Anderson et al. |
| 2004/0193021 A1 | 9/2004 | Zdeblick et al. |
| 2005/0192652 A1 | 9/2005 | Cioanta et al. |
| 2006/0069306 A1 | 3/2006 | Banik et al. |
| 2007/0016163 A1 | 1/2007 | Santini et al. |
| 2007/0021713 A1 | 1/2007 | Kumar et al. |
| 2007/0060915 A1 | 3/2007 | Kucklick |
| 2007/0217933 A1 | 9/2007 | Haser et al. |

(56) References Cited

U.S. PATENT DOCUMENTS

| | | |
|---|---|---|
| 2007/0249993 A1 | 10/2007 | Mollstam et al. |
| 2008/0077128 A1 | 3/2008 | Woloszko et al. |
| 2008/0154095 A1 | 6/2008 | Stubkjaer et al. |
| 2008/0319382 A1 | 12/2008 | Blank et al. |
| 2009/0036914 A1 | 2/2009 | Houser |
| 2009/0187131 A1 | 7/2009 | Fitzgerald et al. |
| 2010/0076372 A1 | 3/2010 | Hacker et al. |
| 2010/0152724 A1 | 6/2010 | Marion et al. |
| 2010/0155465 A1 | 6/2010 | Mollstam et al. |
| 2011/0118695 A1 | 5/2011 | Eckhoff et al. |
| 2011/0152824 A1 | 6/2011 | DiPerna et al. |
| 2012/0035417 A1 | 2/2012 | Mollstam et al. |
| 2012/0116393 A1 | 5/2012 | Jimenez et al. |
| 2012/0215221 A1* | 8/2012 | Woloszko ............ A61B 18/042 606/41 |
| 2012/0253303 A1 | 10/2012 | Suzuki et al. |
| 2012/0310149 A1 | 12/2012 | Van Den Bossche et al. |
| 2013/0116689 A1 | 5/2013 | Marion et al. |
| 2013/0267779 A1 | 10/2013 | Woolford et al. |
| 2013/0267894 A1 | 10/2013 | Woolford et al. |
| 2013/0267947 A1 | 10/2013 | Orszulak |

FOREIGN PATENT DOCUMENTS

| | | |
|---|---|---|
| EP | 1933744 B1 | 12/2010 |
| EP | 1827275 B1 | 8/2011 |

OTHER PUBLICATIONS

Fms duo.RTM.+ Fluid management system, Integrated shaver/pump system, published before Dec. 5, 2006 (4 pages).

"FMS Solo Manual" published before Jan. 2010, pp. 4-30 (27 pages).

"Flosteady Arthroscopy Pump", published Oct. 12, 2012, pp. 1-61 (66 sheets).

Fms solo.RTM. Advanced Irrigation Pump, Irrigation System, published before Dec. 5, 2006 (2 pages).

\* cited by examiner

INTEGRATED PUMP CONTROL FOR DYNAMIC CONTROL OF PLASMA FIELD

CROSS-REFERENCE TO RELATED APPLICATION

This application is a continuation of U.S. application Ser. No. 16/690,418, filed Nov. 21, 2019, (now U.S. patent Ser. No. 11/660,460, which is a divisional of U.S. application Ser. No. 15/292,496, filed on Oct. 13, 2016, which claims the benefit of U.S. Provisional Patent Application No. 62/242,529, filed Oct. 16, 2015, the disclosures of all of which are hereby incorporated by reference in their entirety.

FIELD OF THE INVENTION

This invention relates generally to pump systems and, more particularly, to pumps and pump controlling devices and methods for surgical procedures.

BACKGROUND OF THE INVENTION

Fluid management pump systems are employed during surgical procedures to introduce sterile solution into surgical sites. One such procedure in which a fluid management pump is employed is during an endoscopic surgical procedure. In endoscopic surgery, an endoscope is inserted into the body at the site where the surgical procedure is to be performed. The endoscope is a surgical instrument that provides a view of the portion of the body in which it is inserted. Other surgical instruments are placed in the body at the surgical site. The surgeon views the surgical site through the endoscope in order to manipulate the other surgical instruments. The development of endoscopes and their companion surgical instruments has made it possible to perform minimally invasive surgery that eliminates the need to make large incisions to gain access to the surgical site. Instead, during endoscopic surgery, small openings, called portals, are formed in the patient. An advantage of performing endoscopic surgery is that since the portions of the body that are cut open are minimized, the portions of the body that need to heal after the surgery are likewise reduced. Still another advantage of endoscopic surgery is that it exposes less of the interior tissue of the patient's body to the open environment. This minimal opening of the patient's body lessens the extent to which the patient's internal tissue and organs are open to infection.

The ability to perform endoscopic surgery is enhanced by the development of fluid management pumps. A fluid management pump is designed to pump a sterile solution into the enclosed portion of the body at which the endoscopic surgical procedure is being performed. This solution expands and separates the tissue at the surgical site so as to increase both the field of view of the surgical site and the space available to the surgeon for manipulating the surgical instruments. One type of endoscopic surgery in which fluid management pumps have proven especially useful is in arthroscopic surgery. In arthroscopic surgery, a specially designed endoscope, called an arthroscope, is employed to examine inter-bone joints and the ligaments and muscles that connect the bones. A fluid management pump is often employed in arthroscopic surgery to expand the space between the bones and adjacent soft tissue in order to increase the field in which the surgeon can perform the intended surgical procedure. Fluid management pumps are, during arthroscopic surgery, used to increase the surgical view of the joints that form an elbow, a knee, a wrist, or an ankle. Fluid management pumps are used both in endoscopic surgery and in other surgical procedures to remove debris generated by the procedure.

A fluid management pump system includes a number of different components. There is the pump unit that supplies the motive force for pumping the sterile solution through an inflow tube into the surgical site. The actuation of the pump is regulated by a control unit. The control unit receives as input signals both surgeon-entered commands and an indication of the liquid-state fluid pressure at the surgical site. Still another component of a fluid management pump system is the tube set. The tube set includes the fluid communication tubes that are connected between the pump unit, the control unit, and the surgical site in the patient which is infused with the distention fluid. The tube set includes the previously described inflow tube through which the solution is introduced into the surgical site. There is also an outflow tube through which the solution and any waste material carried therewith are removed from the surgical site. Fluid flow from the site can be regulated by a valve integral with the control unit that selectively opens and closes the outflow tube. The tube set also includes a pressure feedback tube. The pressure feedback tube provides a fluid communication path between the surgical site and the control unit so that a pressure transducer integral with the control unit can monitor the fluid pressure at the surgical site. The pressure signal the transducer supplies is used by the control unit to regulate the actuation of the pump unit and to control the open/closed state of the fluid outflow tube.

Most fluid management pump systems further include cannulae that are inserted into the patient. The cannulae function as the actual fluid communication paths between the surgical site and the tubes forming the tube set. In order to minimize the number of portals that need to be formed in the patient, a single cannula can be provided that provides both the fluid communication into the body for the inflow tube and the pressure feedback tube that functions as the guide bore through which the endoscope is inserted. These particular cannulae are called pressure sensing cannulae. An RF probe, shaver or other instruments may be used in the endoscopic surgical procedure, along with the fluid management pump. These instruments may provide information to the control unit of the pump, which can then be used to control one or both of the inflow or outflow to the pump, based on the desired conditions of the surgical site. One such condition is a plasma field which is advantageous when in a stable condition. An algorithm used by the control unit of the pump can control inflow and outflow rates to achieve a stable plasma field.

Other advantages, objects and/or purposes of the invention will be apparent to persons familiar with constructions of this general type upon reading the following specification and inspecting the accompanying drawings.

For purposes of description herein, it is to be understood that the invention may assume various alternative orientations, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
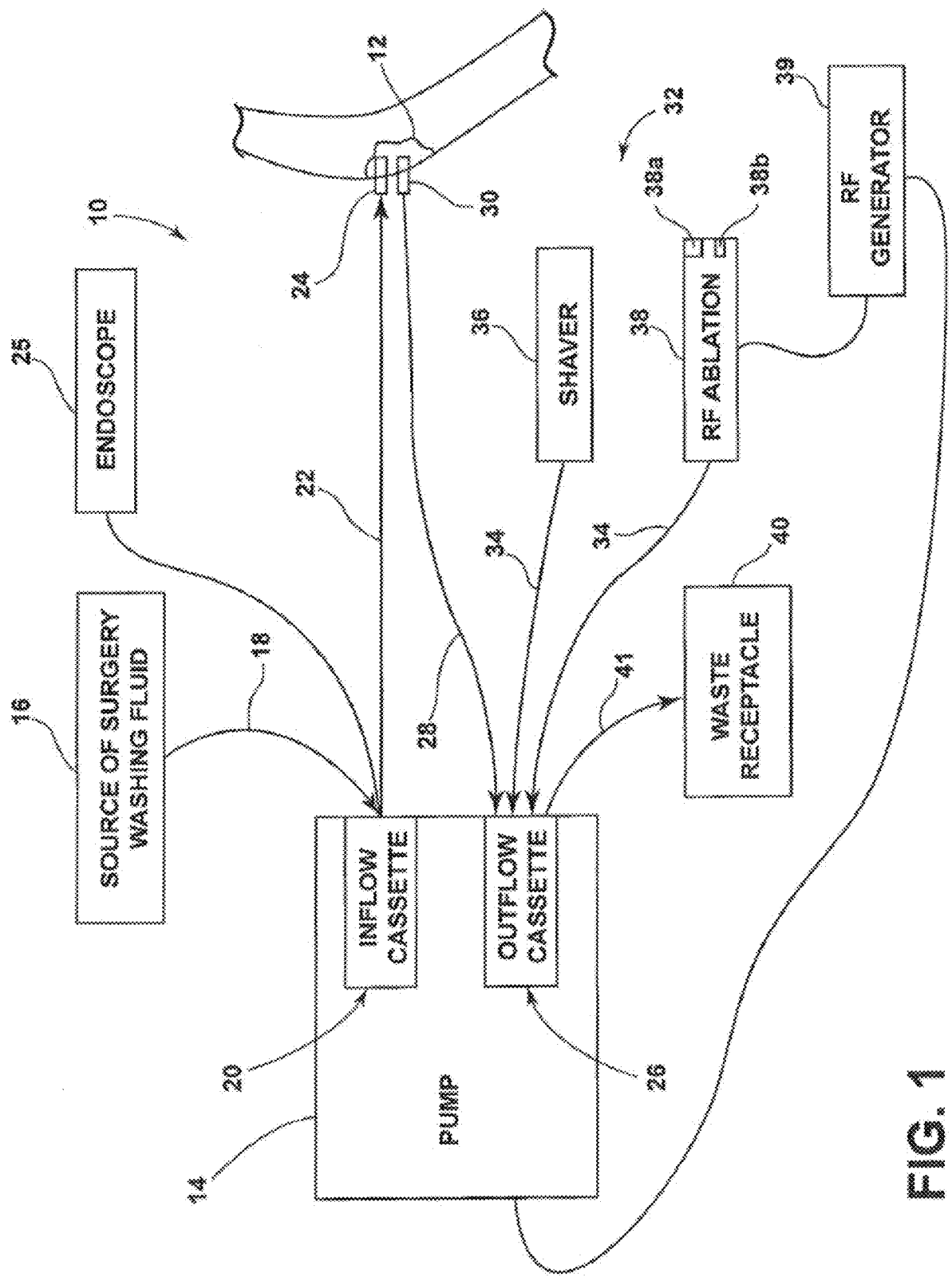
FIG. 1 is a schematic view of a pump system of the present invention illustrating flow paths through the pump system.

Referring to FIG. 1, there is illustrated a pump system 10 and flow paths through the pump system 10. The pump system 10 includes a pump 14 configured to provide a surgery washing fluid to a body cavity 12 (e.g., a joint) during surgery and to suction waste fluid out of the body cavity 12.

As illustrated in FIG. 1, the pump 14 receives a surgery washing fluid from a source of surgery washing fluid 16. The surgery washing fluid could be any washing fluid used in surgery and could be, for example, 0.9% saline or Ringer's lactate. The surgery washing fluid can provide irrigation to the body cavity 12, provide distension in a joint to give a surgeon room to operate in certain joints, and/or provide tamponade to help with bleeding. Input tubing 18 is connected between the source of surgery washing fluid 16 and the pump 14 for supplying the surgery washing fluid to the pump 14. As illustrated in FIG. 1, the pump 14 can have an inflow cassette 20 inserted therein for receiving the surgery washing fluid and for pushing the surgery washing fluid to the body cavity 12 through an inflow tube 22. Typically, the inflow tube 22 is inserted into and/or connected to an inflow cannula 24 inserted into the body cavity 12.

The illustrated pump 14 can also have an outflow cassette 26 inserted therein for suctioning the fluid out of the body cavity 12. An outflow tube 28 extends between the body cavity 12 and the outflow cassette 26, with the outflow tube 28 typically inserted into and/or connected to an outflow cannula 30 inserted into the body cavity 12. The outflow cassette 26 can also have one or more surgery devices 32 connected thereto by device suction tubing 34. The surgery devices 32 are configured to suction the fluid out of the body cavity 12 while the surgery devices 32 are being used within the body cavity 12. The surgery devices 32 can include a shaver 36, an RF device 38 or any other surgery device that can suction waste fluid out of the body cavity 12. The RF device 38 has at least one electrode 38a which can generate a plasma field. The RF device 38 also preferably has a fluid port 38b. An RF generator 39 is connected to the RF probe 38 and to the pump 14. The RF generator 39 provides feedback to the pump 14, which is used in determining the outflow from the pump 14.

The outflow cassette 26 is connected to a waste receptacle 40 by waste tubing 41. The outflow cassette 26 works with the pump 14 to suction the waste fluid out of the body cavity 12 and to push the waste fluid into the waste receptacle 40 through the waste tubing 41. The input tubing 18, the inflow tube 22, the outflow tube 28, the device suction tubing 34, and the waste tubing 41 can have any length.

In the illustrated example, the pump system 10 can receive information from all elements of the pump system 10 to change the flow rate and/or pressure of the surgery washing fluid being provided to the body cavity 12 (i.e., inflow characteristics) and/or to change the flow rate and/or pressure of the waste fluid being suctioned from the body cavity 12 (i.e., outflow characteristics). In the illustrated example, the pump 14 and/or an integration system can contain an algorithm for altering the inflow and/or outflow characteristics. Therefore, while most of the information paths are illustrated as being between the pump 14 and other elements, the information paths could lead to the integration system instead of the pump 14. In some embodiments, the integration system is disposed within a pump housing. The pump 14 and/or integration system can include information from the body cavity 12 (e.g., pressure and temperature within the body cavity 12), the surgery devices 32 (e.g., voltage, impedance, power, current at the surgical site via the shaver 36 and/or the RF probe 38), the RF generator 39, a foot pedal, a remote control, inflow information measured within the pump 14 including pressure information of the fluid outputted from the pump 14, and outflow information measured within the pump 14 including pressure information of the fluid suctioned by the pump 14. The pump 14 can also include an input device for inputting information directly into the pump 14 (e.g., a keyboard or touch screen).

Figure 2:
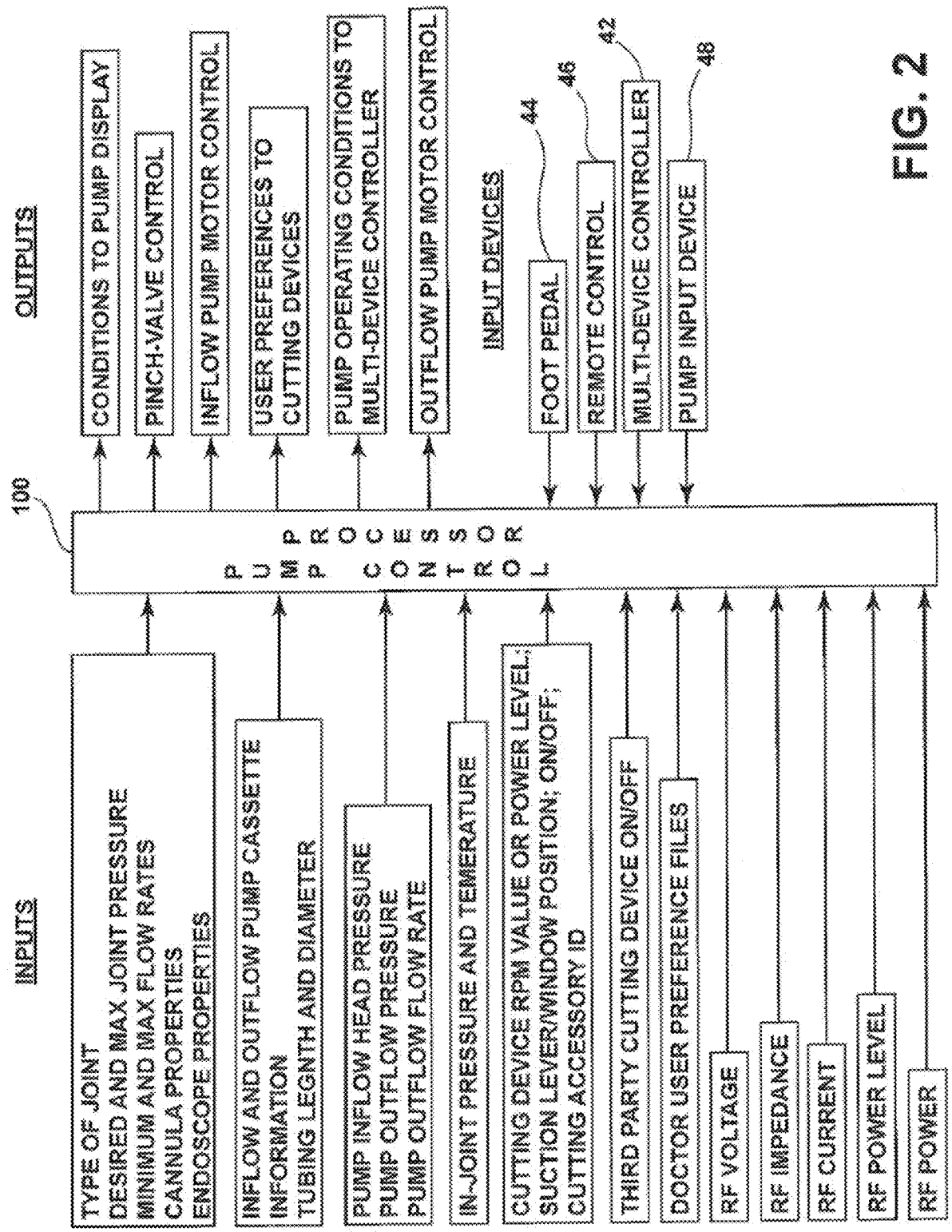
FIG. 2 is a block diagram showing inputs provided to the pump control processor and outputs from the pump control processor.

FIG. 2 illustrates various inputs, outputs and input devices that are provided with a pump control processor 100. The pump control processor 100 uses various input data to determine and control the flow of solution from the pump 14. The input devices include the multi-device operating room controller 42, a foot pedal 44, a remote control 46, and a pump input device 48.

In various embodiments, only some of the inputs shown in FIG. 2 are provided to the pump control processor 100 and only selected ones of the outputs are output therefrom. For example, in some embodiments of the invention there is no outflow pump motor control. In other embodiments, an unidentified third party surgical device is provided, wherein the pump control processor 100 does not know device parameters of such a surgical device. Many embodiments of the invention do not include an in-joint pressure sensor or an in-joint temperature sensor, and thus such directly measured joint pressure values are not provided to the pump control processor 100. In some embodiments, a multi-device operating room controller is not connected to the pump system 10. Further, additional inputs and outputs for the pump control processor 100 that are not shown in FIG. 2 are also contemplated.

Identified Components:

In one embodiment, the type of inflow cannula 24, type of endoscope 25, and the type of inflow tube 22 and length thereof are identified. Identification information for each of the components is input into the pump control processor 100 manually or automatically. The dimensions and length of the inflow and outflow tubing, along with other properties, is typically automatically read by RF communication or identified by the pump control processor 100 when inflow and outflow tubing, via cassettes or otherwise, is inserted into the pump 14.

The pump control processor 100 utilizes stored or read dimensions and other values for the known identified components to calculate a pressure loss ($P_{loss}$) curve based on the dimensions and characteristics of the inflow tubing 22, the inflow cannula 24 and the endoscope 25 that define an inflow path to the surgical site 12 in the joint. Details for the inflow tubing, the endoscope 25 and the inflow cannula 24 can be stored in pump memory. An algorithm or program executed by the pump control processor 100 calculates coefficients ($COEF_1$ and $COEF_2$) defining the $P_{loss}$ curve from the properties including the dimensions and length of the tubing 22, and properties including dimensions of both the cannula 24 and the endoscope 25. The coefficients are provided in an equation including speed or velocity, typically revolutions per minute (RPMs) of an inflow pump motor to calculate a $P_{loss}$ value at a point on the $P_{loss}$ curve as defined for a given inflow pump motor speed.

Obtaining a $P_{loss}$ value on the $P_{loss}$ curve for an RPM value of the inflow pump motor requires an algorithm or program calculating a second order polynomial using the load coefficients $COEF_1$, $COEF_2$ as set forth in the following equation:

$$P_{loss}=COEF_1 \times (RPM\ value)^2 + COEF_2 \times (RPM\ value)$$

The above pressure loss equation results in a calculated $P_{loss}$ value at a given RPM value for the inflow motor of the pump system.

A measured head pressure ($P_{head}$) sensed by a pump inflow pressure sensor of the pump 14 disposed at or near the inflow pump cassette 20 may be used to calculate the in-joint pressure using the following equation:

$$P_{joint}=P_{head}-P_{loss}$$

Using the above calculation, the pump control processor 100 may control the inflow pump motor to maintain the $P_{joint}$ value at a generally constant predetermined desired pressure value regardless of the outflow arrangement.

The pump control processor 100 controls the inflow pump motor over a range in which there is a linear relationship between the flow rate and the inflow pump motor RPM value using the following equation:

$$Inflow=COEF_{INFL} \times (RPM\ value)$$

The inflow coefficient $COEF_{INFL}$ value is loaded from a look-up table for the identified hardware (cannula, inflow tubing, etc.) connected to the pump.

In some embodiments, an inflow cannula provides fluid to a joint without an endoscope. In such an instance, the pump control processor 100 simply determines the load coefficients and inflow coefficient from the inflow tubing and the inflow cannula. In other embodiments the cannula is an outflow cannula or a different cannula.

Unidentified Components:

Another embodiment of an inflow pump control arrangement is utilized wherein the dimensions and other properties of the inflow tubing 22, inflow cannula 24, and the endoscope 25 are unknown. In this embodiment, the pump control processor 100 utilizes a calibration routine or an algorithm as a start-up pump priming routine to obtain data values that are used to calculate the pressure loss coefficients $COEF_1$ and $COEF_2$ that define a $P_{loss}$ curve. At start-up, the pump priming routine begins. Such a routine is described in U.S. patent application Ser. No. 13/782,660, filed Mar. 1, 2013, which published as U.S. Publication No. 2013/0267779, and which is hereby incorporated by reference in its entirety. The pressure loss equation thus results in a calculated pressure loss $P_{loss}$ for a pump system having an unidentified tubing size and length, an unidentified endoscope and an unidentified cannula disposed between the pump and the surgical site of a joint.

Unlike the first embodiment discussed above, wherein the hardware such as the endoscope, the cannula, and the tubing are identified, in this embodiment pump priming execution is necessary to determine the coefficients $COEF_1$, $COEF_2$ for the second order polynomial equation defining a $P_{loss}$ curve.

Unlike the first embodiment, wherein the inflow coefficient $COEF_{INFL}$ is determined from the identified hardware, $COEF_{INFL}$ is determined from a look-up table in view of the values of coefficients $COEF_1$, $COEF_2$. In some embodiments, properties of the inflow tubing 22 may be obtained by the pump control processor 100 from the inflow pump cassette before start-up.

Recognized Surgical Device:

Surgical devices 32 manufactured by the manufacturer of the pump system 10 recognize each other's signals and thus are capable of two-way communication. Thus, performance parameters of surgical devices 32 and cutting accessories can be communicated to the pump control processor 100. In some embodiments for the shaver 36, parameters including shaver identification information and identification information including the type and size of bur or other surgical device accessory disposed on the shaver is provided automatically to the pump control processor 100. Further, the ON/OFF condition, the specific cutter or bur used, the type of operating mode selected for the shaver (examples are Forward, Reverse, Oscillation, etc.), the real-time RPM value of a shaver motor during operation, and other properties can be provided to the pump control processor 100 via the communication bus to optimize the performance of the pump 14. Further, a window size and window position of a surgical device and/or cutting accessory can be provided to the pump control processor 100.

In some embodiments, the dimensions of a flow path through a surgical device handpiece and the position of a lever controlling flow through the path can be provided over the communication bus to the pump control processor 100. In some embodiments surgical device identifiers and cutting accessory identifiers are sent over the communication bus to the pump control processor 100 and values for the bur size, window size, and flow path dimensions that are previously stored in the pump memory can be retrieved.

Figure 3:
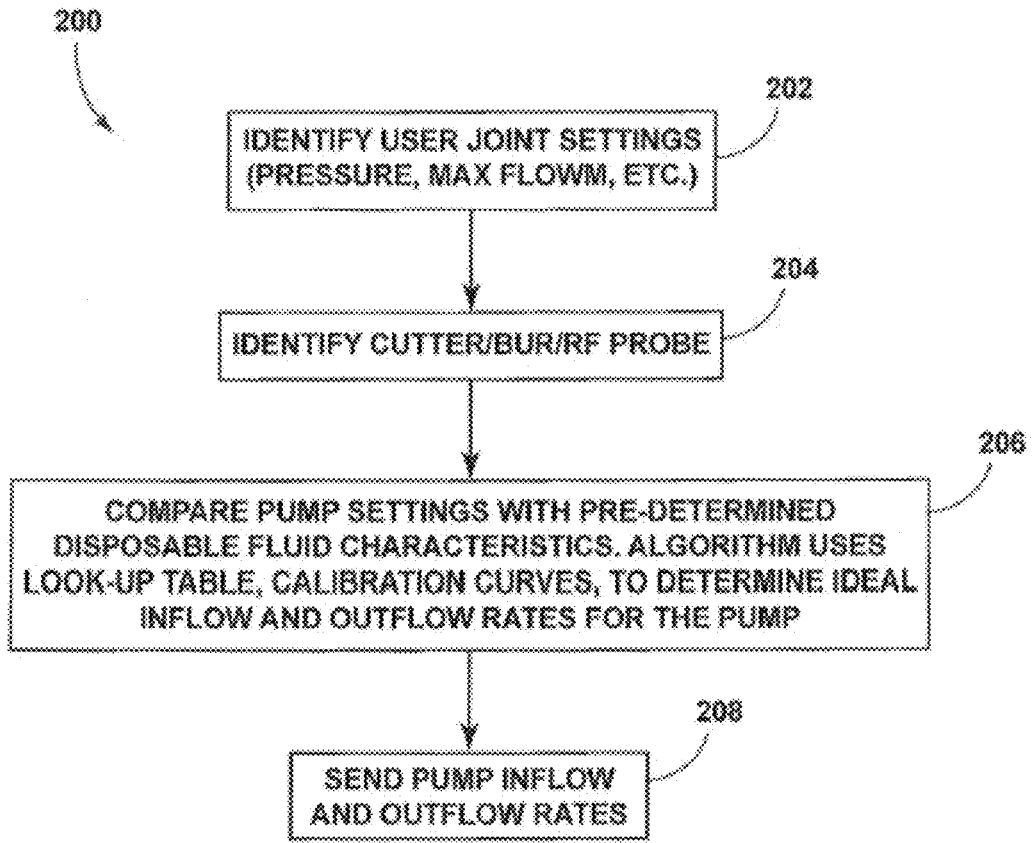
FIG. 3 is a flowchart of a portion of a pump system operating routine that includes obtaining information regarding a cutting accessory.

FIG. 3 is a flowchart of the steps of a portion of a pump flow control routine 200 executed by the pump control processor 100 that emphasizes the identification of a cutting accessory. At step 202, the type of joint, maximum and minimum flow rates, a desired or best flow rate that minimizes fluid consumption and maintains good visibility, a maximum pressure value, a desired pressure value and other types of information, including but not limited to the information or parameters listed and shown in FIG. 2, can be provided to the pump control processor 100. The information can be manually entered into the pump control processor 100 via an input device, read or downloaded automatically from a memory card or the like, or provided by other means. Then the routine advances to step 204.

At step 204 surgical device information, including identification information for a cutting accessory attached thereto, is provided to the pump control processor 100. As discussed above, the information can be provided over a communication bus. The surgical device 32 can include an RF reader to identify an RF tag secured to the cutting accessory. In another embodiment, the pump includes an RF reader to identify RF tags secured to both the surgical device and the cutting accessory. The routine then advances to step 206.

At step 206, the routine or program executed by the pump control processor 100 compares pump settings with predetermined disposable fluid flow characteristics. An algorithm or program uses a look-up table, calibration curves, and in some embodiments additional information to determine ideal fluid inflow and fluid outflow rates for operation of the pump 14. At step 208, the pump inflow control signals, and in some instances outflow information, is provided to the inflow pump motor and to additional devices to obtain ideal in-joint pressures and fluid flow at the surgical site.

A feedback path (not shown) from step 208 returns to a program or routine whereat an algorithm recalculates pump flow rates based on one or more of real-time joint pressure, inflow head pressure, pump motor speeds, surgical device speed, and ON/OFF condition. Typically, the routine does not need to re-identify the surgical device or the cutting accessory. Further, the user joint settings, such as desired joint pressure, maximum and minimum joint pressure, maximum and minimum fluid flow through the joint, and desired fluid flow information typically do not change, and thus the routine typically does not return to step 202 until one cutting operation ends and another cutting operation begins.

In one example, for a shaver operating at a motor speed of 12,000 RPM with a 5.0 mm round bur attached thereto, and a desired pressure value of 70 mmHg, the algorithm or routine executed by the pump control processor 100 provides outputs to the inflow pump motor, the outflow pump motor, and in some instances to other devices including outflow pinch valves, to obtain the desired joint pressure of 70 mmHg, while maintaining desirable inflow and outflow rates for the pump output.

When the shaver 36 is operated, the pump control processor 100 receives the ON/OFF condition and the RPM output value of the shaver and calculates and controls the inflow pump RPM value that is output by the inflow pump motor, controls the outflow pump motor, and controls pinch valves provided with or near an outflow cassette by opening a valve for the outflow tubing 34 connected to the shaver while closing a separate outflow tubing 28 from the outflow cannula 30.

The additional surgical device information, along with the joint pressure values calculated or sensed as described above, enable the pump control processor 100 of the pump 14 to more accurately control the $P_{joint}$ value and fluid flow rates that result in surgical site conditions that closely correspond to the selections or inputs of an authorized medical user operating the pump system 10.

As the shaver is identified, a non-linear outflow rate to RPM curve is provided with a look-up table containing coefficients to predict the outflow rate based on the outflow RPM for controlling the pump to provide a desired or best outflow rate. This is also the procedure for a recognized RF probe.

User preferences and other information from the pump control processor 100 can be provided to the surgical device 32, such as the shaver 36 and RF ablation device 38. The preferences can include surgical device settings preferred by the medical user that will be operating the surgical device 32 and the pump system 10.

Unrecognized Shaver and RF Ablation Surgical Devices:

The pump 14 can be utilized with unrecognized third-party surgical devices 32 that are not identifiable by the pump control processor 100. Such RF ablation devices and shaver devices are typically connected to power outlets located on the backside of the pump housing. Located within the pump housing are current and/or voltage sensing devices that sense a current waveform of the power drawn by the unrecognized surgical devices when operated. Instantaneous and past changes in the current waveform can be normalized to changes in the applied mains voltage and the pump control processor 100 can execute a linear-discrimination algorithm to optimally differentiate between times when the unidentified surgical devices are off and when the surgical devices are activated to treat or cut tissue.

As discussed above, the critical flow rate values and maximum pressure value for the surgical site 12 at the joint are typically different during operation of a surgical device 32 as compared to during non-operation of the surgical device. Therefore, sensing surgical device activation enables adjustments to the desired joint pressure value and fluid flow by control of the inflow pump motor, outflow pump motor and other devices while the surgical device is activated.

In-Joint Sensor:

In some embodiments an in-joint sensing device includes an in-joint pressure sensor and/or an in-joint temperature sensor that are disposed at or adjacent the surgical site. The in-joint sensing device can obtain and send a real-time pressure value from the surgical site 12 to the pump control processor 100, thereby avoiding reliance on the calculated $P_{loss}$ curves discussed above. The in-joint sensing device also reduces time delay in determining pressure changes in the joint. For instance, when pressure changes are measured upstream, there is a delay in the pressure change at the joint propagating through the inflow tubing to the sensor in the pump 14. The in-joint pressure sensor also removes the upstream pressure measuring influence of hydrostatic head which occurs due to height differences between the pump and the cutting accessory located at the surgical site. Therefore, the pump need not be maintained at the same level or height as the surgical site.

Overpressure:

Regardless of the type of $P_{joint}$ calculation or direct pressure measurement, a $P_{joint}$ value must not exceed a predetermined pressure value. Thus, when an overpressure condition is calculated or measured, the pump control processor 100 performs at least one of operating outflow pinch valves, reducing the RPM value of the inflow pump motor, and other steps to reduce the joint pressure.

Plasma Field Stability:

It has been found that when certain electrical characteristics are not maintained at a threshold level (or within a certain range), significant instability in a plasma field can occur at the surgical site. The stability of the plasma field is significantly influenced by the suction rate through a probe. Higher flow rates tend to show more instability in the plasma field. Accordingly, stability thresholds can be determined for each different type of probe, and the pump 14 can dynamically control the suction rate in order to maintain the electrical characteristic value above the stability threshold, while having a goal of keeping the suction rate as high as possible while maintaining stability of the plasma field.

The pump control processor 100, via the RF probe 38, measures one or more of the electrical characteristic values of the RF probe 38 when activated. Through integration with the pump 14, the electrical characteristics of the RF probe 38 can be delivered to the pump 14 in real time.

Figure 4:
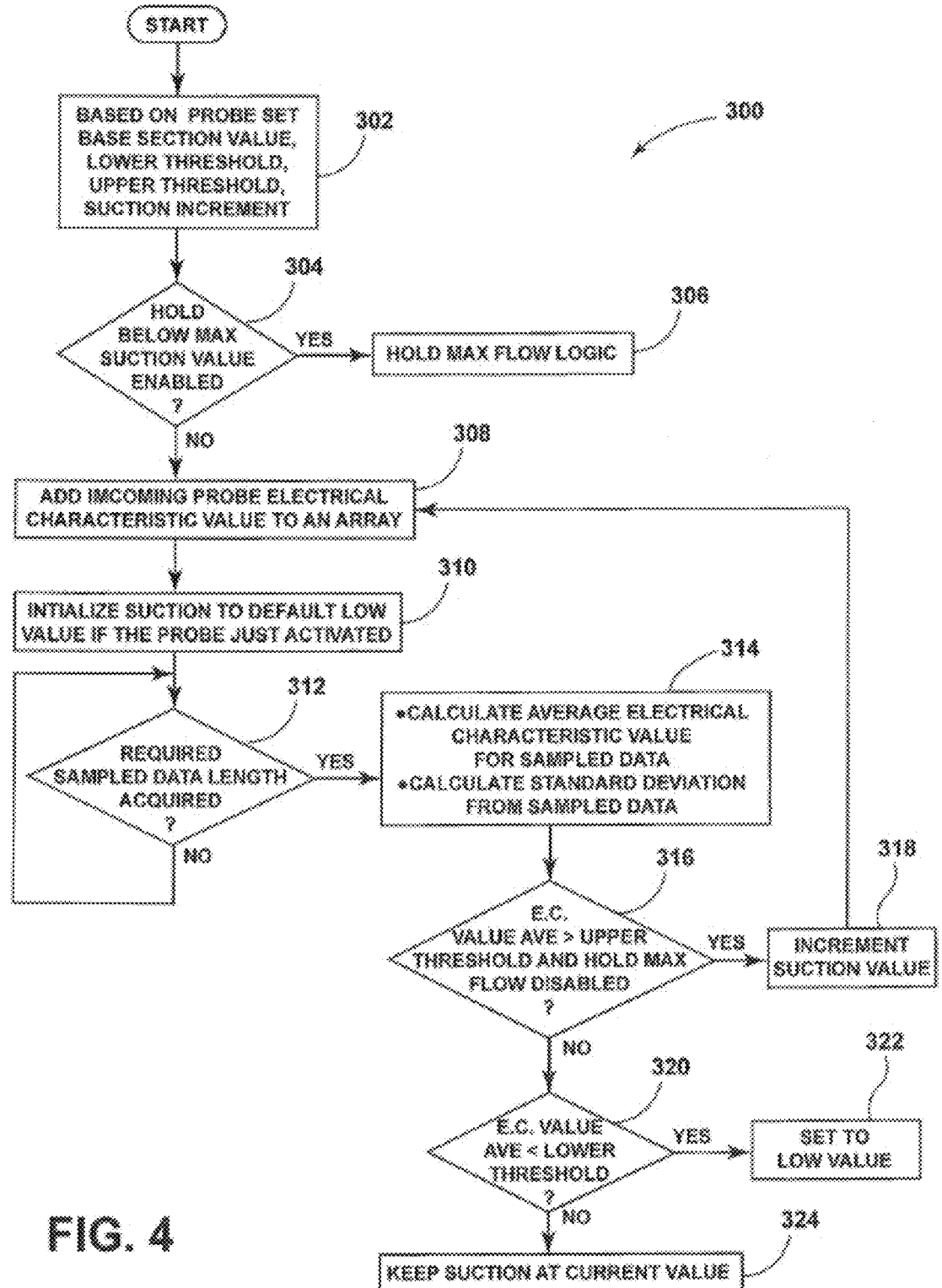
FIG. 4 is a flowchart of a portion of a pump system operating routine to adjust the suction in a surgical pumping system.

In one embodiment, an algorithm or routine, as shown in FIG. 4, is utilized to attempt to maintain a stable plasma field. The suction level achieved by the pump 14 starts at a low value when the RF probe 38 is activated, and the pump system 10 samples the electrical characteristic value(s) for the activated probe.

Specifically, once the algorithm is started, based on the probe type, the controller 100 sets variables of a base suction value, a lower threshold electrical characteristic value, an upper threshold electrical characteristic value, and a suction increment value (step 302). The algorithm then moves on to the step of determining whether it should hold the suction value below the maximum value (step 304). If the answer to this question is YES, then the algorithm moves to step 306 at which the max flow logic is held. If the answer to step 304 is NO, then the algorithm moves to step 308 at which the incoming probe electrical characteristic value is assigned to an array. The algorithm then moves to step 310, at which if the probe has just been activated, the suction value is changed to a default low value, which may be zero.

The algorithm then moves on to step 312 at which it is determined whether the required length of time has been met for sampling data. If the answer to this question is NO, then the system continues to acquire data sampling until the required time value is met. Once the required time length has been achieved for sampling data, the algorithm moves to step 314, at which an average electrical characteristic value is calculated for the sampled data. A standard deviation for the sampled data is also calculated.

Once the average electrical characteristic value and standard deviation are calculated, the algorithm moves to step 316, at which it is determined whether the average electrical characteristic value is greater than the upper threshold voltage value and whether the hold max flow has been disabled. If the answer to both of these questions is YES, then the algorithm moves to step 318 at which the suction rate is increased by the suction increment value. The algorithm then goes back to step 308 to add the incoming electrical characteristic value to an array and the data is sampled again. If the answer to either of the questions of step 316 is NO, the algorithm moves to step 320, at which it is determined whether the average electrical characteristic value is less than the lower threshold electrical characteristic value. If the electrical characteristic value average is less than the lower threshold electrical characteristic value, then the algorithm moves to step 322, at which the suction is set to the base suction value. If the answer to the question of step 320 is NO, the algorithm moves to step 324 to maintain the suction at the same level.

In another embodiment, instead of at step 322 setting the suction to a low, base value, the suction rate is incrementally decreased based either on the suction increment value assigned at step 302, or a second suction increment value.

In another embodiment, the suction rate may be increased depending on the actual value measured. Thus, instead of having a fixed incremental increase, the increase in flow rate is calculated using a particular function depending on the actual value of an electrical characteristic, such as voltage, which may allow the suction rate to increase more when needed, but not at other times.

The algorithm 300, and in particular the electrical characteristic reading and sampling, could also be used to determine if the system is clogged with tissue and could help with declogging the system. When a probe is clogged, the sampled electrical characteristic sustains a value above an upper threshold which causes the algorithm to increase the suction to the maximum value very quickly. This sustained maximum value can be used as an indicator that the probe is clogged.

A similar algorithm could use the information that the probe is clogged to have the pump try a number of different methods to declog the probe, such as pulsing the outflow suction, increasing the joint pressure, and increasing the outflow motor RPMs beyond a set limit to attempt to achieve a higher suction.

The algorithms and system described herein improves the RF device performance and may reduce clogging. Performance of the system is improved by maintaining a more stable plasma field as the surgeon resects tissue.

Although particular preferred embodiments of the invention have been disclosed in detail for illustrative purposes, it will be recognized that variations or modifications of the disclosed apparatus, including the rearrangement of parts, lie within the scope of the present invention.

The invention claimed is:

1. A method of controlling a surgical pump system, the method comprising the steps of:
    providing a pump system for motivating fluid to and from a surgical site during a surgical procedure;
    providing a pump controller connected to the pump system for controlling a fluid flow rate inflow to the surgical site and for controlling suction of the fluid from the surgical site;
    providing a surgical device for performing the surgical procedure, the surgical device having an associated electrical characteristic value at a given time; and
    the pump controller performing the following steps:
        (a) retrieving and recording a sampling of surgical device electrical characteristic values during a sample duration;
        (b) determining whether the sampled duration has met a predetermined length of time;
        (c) calculating an average electrical characteristic value based on the sampling of the surgical device electrical characteristic values if the sampled duration has met the predetermined length;
        (d) modifying an amount of the suction if the average electrical characteristic value is outside a predetermined range.

2. The method of claim 1, further comprising providing the predetermined range between a predetermined upper threshold electrical characteristic value and a predetermined lower threshold electrical characteristic value and communicating the predetermined upper threshold electrical characteristic value and the predetermined lower threshold electrical characteristic value to the pump controller.

3. The method of claim 1, further comprising providing a low suction amount value and communicating the low suction amount value to the pump controller.

4. The method of claim 3, wherein the step of modifying the amount of the suction comprises decreasing the amount of the suction to the low suction amount value.

5. The method of claim 4, wherein a low suction amount level is maintained until the pump controller detects a stable plasma field.

6. The method of claim 3, wherein the amount of the suction is modified to a rate not less than the low suction amount value.

7. The method of claim 1, wherein the step of modifying the amount of the suction includes increasing the amount of the suction if the average electrical characteristic value is greater than a predetermined upper threshold electrical characteristic value.

8. The method of claim 1, wherein the step of modifying the amount of the suction includes decreasing the amount of the suction if the average electrical characteristic value is less than a predetermined lower threshold electrical characteristic value.

9. The method of claim 1, further comprising the step of initializing a suction value to zero if the surgical device was just activated.

10. The method of claim 1, further comprising the step of the pump controller setting a suction increment value.

11. The method of claim 10, wherein the step of modifying the amount of the suction comprises increasing the suction using the suction increment value.

12. The method of claim 10, wherein the step of modifying the amount of the suction comprises decreasing the amount of the suction using the suction increment value.

13. The method of claim 1, wherein if the calculated average electrical characteristic value is inside the predetermined range, the pump controller maintains a current suction rate.

14. The method of claim 1, wherein if the average electrical characteristic value calculated is below the predetermined range, then a suction rate is incrementally decreased until a stable plasma field is achieved.

15. A method of controlling a surgical pump system, the method comprising the steps of:
providing a pump system for motivating fluid to and from a surgical site during a surgical procedure;
providing a pump controller connected to the pump system for controlling a fluid flow rate inflow to the surgical site and for controlling suction of the fluid from the surgical site;
providing a surgical device for performing the surgical procedure, the surgical device having an associated electrical characteristic value at a given time;
retrieving and recording a sampling of surgical device electrical characteristic values during a sample duration;
determining whether the sampled duration has met a predetermined length of time;
calculating an average electrical characteristic value based on the sampling of the surgical device electrical characteristic values if the sampled duration has met the predetermined length;
modifying an amount of the suction if the average electrical characteristic value falls outside a predetermined range.

16. The method of claim 15, further comprising providing the predetermined range between a predetermined upper threshold electrical characteristic value and a predetermined lower threshold electrical characteristic value and communicating the predetermined upper threshold electrical characteristic value and the predetermined lower threshold electrical characteristic value to the pump controller.

17. The method of claim 15, further comprising providing a low suction amount value and communicating the low suction amount value to the pump controller.

18. The method of claim 15, wherein a low suction amount level is maintained until the pump controller detects a stable plasma field.

19. The method of claim 15, wherein the step of modifying the amount of the suction includes increasing the amount of the suction if the average electrical characteristic value is greater than a predetermined upper threshold electrical characteristic value.

20. The method of claim 15, wherein the step of modifying the amount of the suction includes decreasing the amount of the suction if the average electrical characteristic value is less than a predetermined lower threshold electrical characteristic value.

* * * * *